United States Patent [19]

Schindler et al.

[11] Patent Number: 4,629,687
[45] Date of Patent: Dec. 16, 1986

[54] POSITIVE SELECTION SORTING OF CELLS

[75] Inventors: Melvin S. Schindler, Okemos; John F. Holland, Lansing, both of Mich.

[73] Assignee: Board of Trustees of Michigan State University, East Lansing, Mich.

[21] Appl. No.: 403,154

[22] Filed: Jul. 29, 1982

[51] Int. Cl.$^4$ .......................... C12N 5/00; C12M 1/34; C12Q 1/00

[52] U.S. Cl. ........................................ 435/4; 435/240; 435/291

[58] Field of Search ...................... 356/39, 73; 422/52, 422/68, 22; 436/63, 172; 250/458.1, 461.1, 461.2, 222.2, 239, 304, 361 R, 461, 492.2, 564, 574, 575; 435/4, 6, 29, 30, 39, 173, 241, 245, 297, 310, 800, 808, 311, 291, 261; 209/3.1, 3.3, 44.1, 540, 541, 552, 578, 579, 644, 906, 932, 934

[56] References Cited

U.S. PATENT DOCUMENTS

| | | |
|---|---|---|
| 3,712,746 | 1/1973 | Bergeron .............................. 435/808 |
| 3,813,544 | 5/1974 | Franzen et al. ...................... 250/281 |
| 3,941,670 | 3/1976 | Pratt, Jr. ................................. 422/22 |
| 3,984,307 | 10/1976 | Kamentsky et al. .................. 356/39 |
| 4,045,772 | 8/1977 | Bouton et al. ......................... 356/39 |
| 4,087,685 | 5/1978 | Froot ..................................... 250/302 |
| 4,090,128 | 5/1978 | Simpson et al. ....................... 356/39 |
| 4,090,921 | 5/1978 | Sawamura et al. .................. 435/808 |
| 4,172,227 | 10/1979 | Turer et al. ....................... 250/461.2 |
| 4,175,662 | 11/1979 | Zöld ..................................... 209/552 |
| 4,204,117 | 5/1980 | Aberle et al. ..................... 250/461.2 |
| 4,209,256 | 6/1980 | Faulkner ................................ 356/73 |
| 4,284,897 | 8/1981 | Sawamura et al. .............. 250/461.2 |
| 4,326,934 | 4/1982 | Pohl . |
| 4,354,114 | 10/1982 | Karnaukhov et al. ........... 250/461.2 |
| 4,395,397 | 7/1983 | Shapiro ................................ 435/289 |
| 4,513,438 | 4/1985 | Graham et al. ......................... 382/6 |

FOREIGN PATENT DOCUMENTS

| | | |
|---|---|---|
| 80/00188 | 2/1980 | PCT Int'l Appl. .................... 422/52 |
| 2100425 | 12/1982 | United Kingdom .................... 435/4 |

OTHER PUBLICATIONS

Higgins et al. 1980 "Selective Cell Destruction & Precise Neurite Transection . . . " J. Neuroscience Methods 3 pp. 83-99.
Mosley et al. 1981 "Targeted Killing of Cultured Cells by Receptor-Dependent Photosensitization" Proc. Natl. Acad Sci 78 pp. 5717-5721.
Lepok et al. 1979 "Photoinduced Cell Killing and Crosslinking of Fluorescein Conjugated Concanavalin A To Cell Surface Proteins" Biochem Biophys Res Comm V 91 pp. 1157-1165.
Berns et al. 1977 "Continuation of Mitosis . . . " J. Cell Biol. vol. 75 pp. 977-982.
Koppel 1979 "Fluorescence Redistribution After Photobleaching" Biophysical Society vol. 28 pp. 281-292.
*Cell Separation: Methods and Selected Applications,* Pretlow II, T. G. et al., ed., Academic Press, New York, pp. 193-198 (1982).
The Coulter ® Epics ® V System, Brochure, Coulter Electronics, Inc., Rev. Apr. 1982.
Koppel, D. E. Biophysics Journal 28:281-291 (1979).
Berns, Journal Cell Biol. 75, 3, 1975.
Higgins, et al., J. Neurosc. Meth. 3, 1, 1980; Besses in Advances in Biological and Medical Physics, Acad. Sci 78, 9, 1981.
8127 Review of Scient. Instr., vol 51, No. 1 (1980,01) New York, pp. 111-115 "Mechanical Cell Separator", Peter Lenz.

*Primary Examiner*—Thomas G. Wiseman
*Assistant Examiner*—Joanne M. Giesser
*Attorney, Agent, or Firm*—Miller, Morriss & Pappas

[57] ABSTRACT

A method and apparatus for positive selection of viable cells based upon differing chemical or physical properties or dynamic processes using a focussed radiant energy beam, such as a laser beam (11) to kill unwanted cells is described. The apparatus includes a microscope (14) with a photomultiplier (27) which is used to selectively detect light from certain cells produced by an attenuated laser beam irradiating the cells for identifying the cells to be killed or saved. Based upon identification, selected cells to be killed are exposed to the unattenuated laser beam.

8 Claims, 6 Drawing Figures

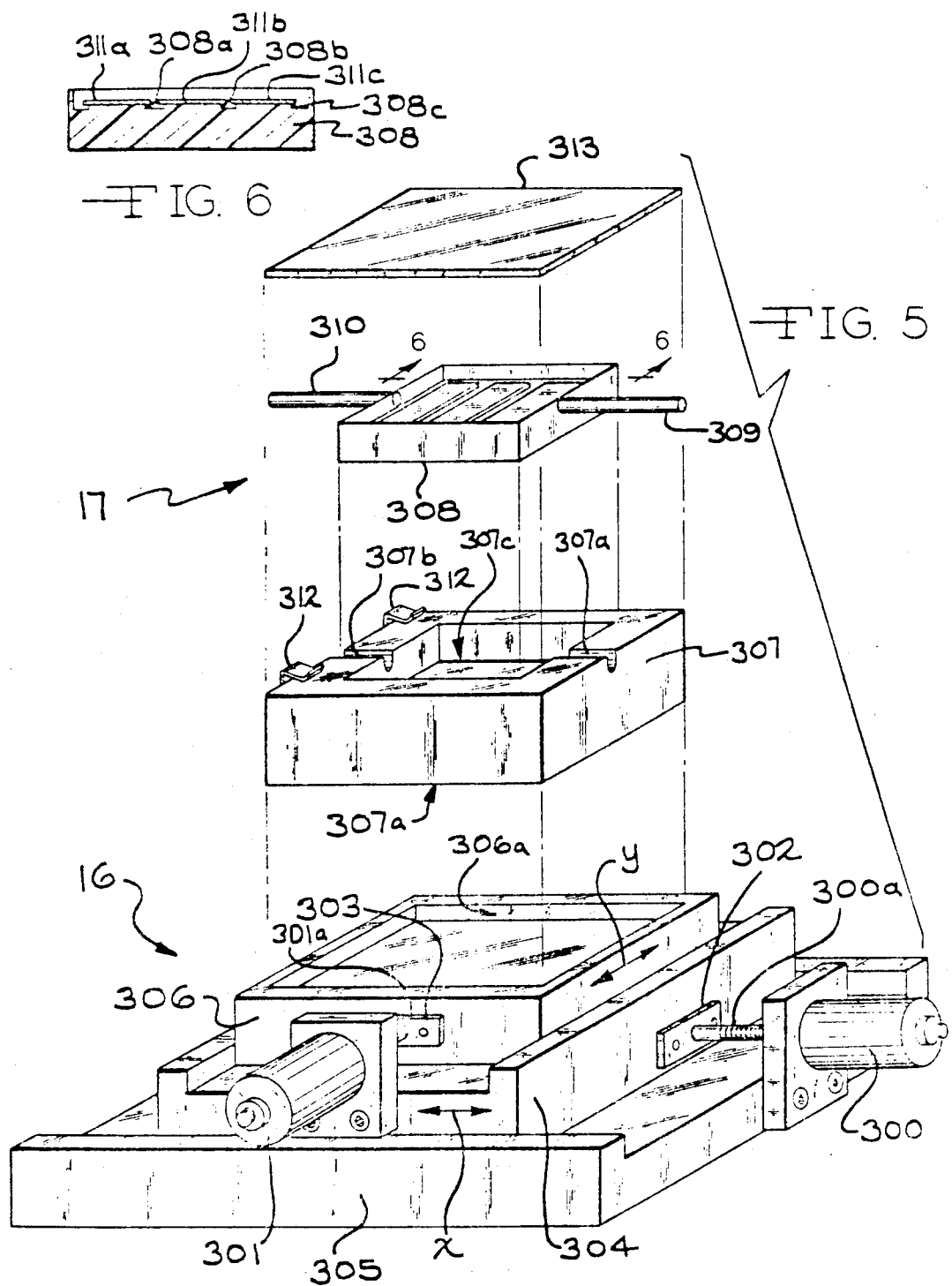

POSITIVE SELECTION SORTING OF CELLS

BACKGROUND OF THE INVENTION

The present invention relates to an apparatus and a method for sorting a population of living cells based upon differing chemical or physical properties or dynamic process capabilities. The method uses a radiant energy beam for destroying unwanted cells in the population.

PRIOR ART

In general in the prior art, a central feature of the chemical analysis of complex mixtures is the isolation and purification of specific compounds. These purified homogeneous components are subsequently characterized with regard to their physical properties. In the past, for cell biochemistry this implied the isolation from the cell of an enzyme or receptor protein by gel chromatography with the attendant destruction of the cell.

With the advent of newer culture techniques and defined media, it has become possible to grow all types of cell lines in culture. This has provided for the possibility of growing sufficient quantities of cells to do biochemical analysis on cell and membrane components. A major problem in this approach, however, is the large variability of cell surface structure leading to altered function within a relatively specific family or population of cells. For example, T-cells of the immune system have sub-populations of cells with altered properties and function. These observations have stimulated researchers to develop methodologies and instrumentation for the purpose of separating the cells into distinct sub-populations on the basis of a defined characterization in a direct analogy to the conceptual approaches of protein separation and purification mentioned above. Mixed polymer systems have been employed to separate cells based on surface properties, cell electrophoresis has been used to separate cells by surface charge, and solid phase lectins and antibodies have been exploited to differentiate between altered structural determinants in membrane proteins for cell separation.

Recently, fluorescence measuring cell sorters have become commercially available. The great advantage of the method and apparatus of these devices is that they efficiently separate a large population of cells based on differences in bound fluorescent probes (usually an antibody or lectin containing a covalently attached fluorophore). Specific selection of parameters are established in these prior art instruments. Cells are sorted into separate tubes based on fluorescent or other light interactive behavioral differences. Sorted cells can be run through the system a number of times to provide further enrichment. In this manner, approximately $1 \times 10^7$ cells, an amount sufficient for characterization, could be sorted in 1 to 2 hours.

The fluorescence activated cell sorter (FACS Systems, Becton Dickinson of Sunnyvale, Calif. U.S.A. and Coulter Electronic, Inc. of Hialeah, Fla.) are computer centered, single laser units capable of analyzing and separating individual cells on the basis of fluorescence, size and viability. The electronic and recording measurements can be made with or without sorting Sorting is accomplished by electrostatic induction on individual cells in a flow system. The laser is used as a light source for the fluorescence The cytofluorographsystem (Ortho Diagnostic Systems, Inc. of Westwood, Mass.) utilizes two laser beams in the same manner and separates again by electrostatic induction based upon mesurements of size, fluorescence and/or refraction indices.

Although this prior art methodology and apparatus represent a major technological breakthrough with regard to obtaining a homogeneous population of cells based upon chemical properties, its usefulness is limited in the following ways:

(1) since all are flow through systems, they are susceptible to the pump and clogging problems observed in any fluid system;

(2) maintaining sterile conditions through long lengths of plastic tubing through which the cells must pass is very difficult;

(3) the buffeting and collisions encountered by cells flowing through the sorter can have deleterious effects on cell membranes, causing unknown cellular responses, in some cases cell death;

(4) Cell differentiation in most instances is determined only by structural markers attached to the cells which does not take advantage of the ability to isolate and separate cells based on altered membrane properties such as the rotational and translational diffusion differences of cell surface components. These parameters have been shown to be important in cell stimulatory events, e.g.—hormones and growth factors;

(5) a major drawback in flow cytometry sorters is the necessity to use cells in suspension for separation. This precludes the use of this technique for the sorting of cells growing in culture mounted on a plate or surface The properties of cells can change dramatically with shape; it is therefore essential to sort them as close to their normal shape as possible. In addition, there has been a strong correlation made between cell shape and ultimate function, both of which are affected by the surface on which the cells grow. Clearly, it would be desirable to separate the cells while growing on specific surfaces This is not possible with the commercial units.

The prior art in Koppel, P. E. et al Biophysics Journal 25:281–291 (1979) has described the use of lasers for irradiating cells mounted on a plate with light energy sufficient to photobleach a spot on a surface of the cell and then to follow the progress of the migration of fluorescently labeled molecules back into the bleached area.

In the Koppel et al apparatus, occasionally the cells can be accidentally killed by the laser beam; however, the apparatus is adapted only for practice of the bleaching method. No provision is made for providing a supply of nutrient medium to the cells and thus there is no means for removing the enzymes and other cell components left in the event the cells are killed. Such components seriously affect the remaining living cells The Koppel apparatus has never been used in a method for cell sorting Other prior art practices include cell or cellular component destruction by laser energy, such as by Higgins, et al., J. Neurosc. Meth., 3, 1, 1980; Bessis in Advances in Biological and Medical Physics, Academic Press, New York; 1970; Mosley, et al , in Proc. Natl. Acad. Sci. 78, 9, 1981; Lepock, et al., Biochem. Biophys. Res. Comm. 91, 3, 1979; and Berns in Jour. Cell Bio. 75,3, 1975.

All of these utilize the destructive power of ultraviolet or coherent radiation for the purpose of destroying selected targets, not for the purpose of cell progeny selection in a life sustaining environment. The application of this prior art involves ablation studies, cell suicide studies (negative selection), Organelle micro-surgery, therapeutic cell destruction and other areas not relating to cell sorting

OBJECTS

It is therefore an object of the present invention to provide a positive selection cell sorting apparatus and method which uses electromagetic radiation beam generating means (10) with attenuator means (12) for the beam for cell destruction for the purpose of cell sorting under the most ideal cell conditions.

Further it is an object of the present invention to provide computer (101) control of the destruction of cells by the beam generating means. It is further an object to provide an apparatus having the ability to sort cells provided on an environmentally controlled plate (17).

It is further an object to provide an apparatus which utilizes cellular properties as well as label recognition as the basis of cell selection.

It is further an object of the present invention to provide an apparatus which has the ability to engage in long term selection processes which can utilize dynamic cellular behavior processes as the basis for cell differentiation.

It is also an object to provide an apparatus which has the ability to use more than one cell paramater as a basis for selection of cells. Such as for example, selection on the basis of a physical characteristic when immature and selection on the basis of a membrane characteristic when mature and including the possibility for multi-dimensional schemes in sequence for more refined selection at any cell stage.

It is an object to provide more effective and efficient sorting processes performed on cells in their natural configuration without perturbation.

It is an object to provide an apparatus which is useful with cell types that are not amenable to the transport selection processes of the prior art Finally it is an object to provide an apparatus which has the ability to monitor without destruction variations in individual cells during incubation where subsequent save or destroy options determine cellular fate.

These and other objects will become increasingly apparent by reference to the following description and the drawings.

IN THE DRAWINGS

FIG. 5 is an isometric exploded view of the plate (17) shown in FIG. 2 showing an x-y moveable stage (16) for the plate.

FIG. 6 is a front cross-sectional view of the plate (17) shown in FIG. 5.

GENERAL DESCRIPTION

Figure 1:
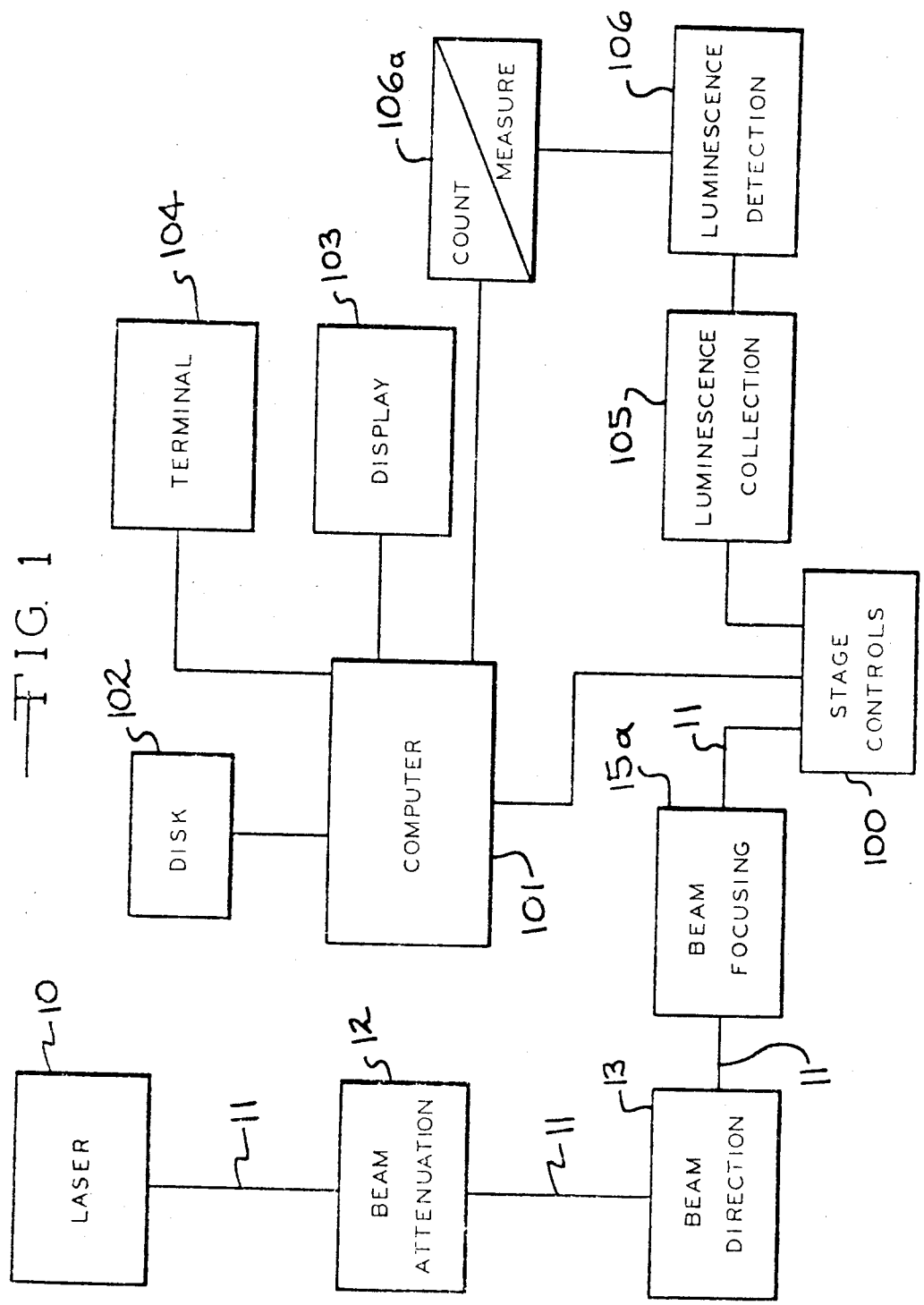
FIG. 1 is a block diagram of the preferred positive selection cell sorting apparatus used in the method of the present invention.

The present invention relates to an apparatus for sorting a heterogeneous population of living cells into a segregated population based upon chemical or physical properties or dynamic processes and then killing unwanted cells which comprises:

microscope means with an objective for scanning a heterogeneous population of cells fixed on a plate positioned adjacent the objective on a coordinate scanning or an individual cell-by-cell scanning basis wherein the plate is adapted to contain a flowing liquid growth medium for the cells;

focussed radiant energy beam generating means associated with the microscope means such that the beam can be focussed in a path through the objective at the plate and at an individual cell or series of cells on the plate; and controlled interruption means for selectively attenuating the beam wherein the beam can kill individual cells on the plate when the interruption means is removed from the path.

The present invention further relates to a preferred apparatus for sorting a heterogeneous population of living cells into a segregated population based upon physical or chemical properties or dynamic processs by killing unwanted cells which comprises:

microscope means with an objective for viewing a heterogeneous population of cells which are fixed on a plate positioned adjacent the objective on a coordinate scanning or an individual cell-by-cell scanning basis, wherein the plate is adapted to contain a flowing liquid growth medium for the cells;

drive means for moving the plate beneath the objective or for moving the objective or beam across the plate in an x-y coordinate plane or for both such that the objective scans all of the cells in the heterogeneous population;

detection means for distinguishing an individual cell based upon a particular chemical or physical property or dynamic processes determined by the detection means through the objective;

focussed radiant energy beam generating means with lenses and mirrors positioned for directing the beam in a path through the objective and at an individual cell or a series of cells viewed by the objective;

attenuator means movable into the beam for selectively attenuating the beam to render it non-lethal;

controlled means for selectively providing the attenuator means into the path of the beam, wherein the detection means distinguishes cells to be saved when the attenuator means is positioned between the objective and the beam by the controlled means and wherein the attenuator means is removed from the path of the beam by the controlled means in order to kill unwanted cells.

The present invention also relates to a method for selectively killing unwanted metabolizing living cells which comprises:

providing the cells on a plate beneath a microscope means with an objective wherein the objective views the cells on an individual cell-by-cell or series of cells basis; and selectively irradiating the individual cells or series of cells with a focussed radiant energy beam through the objective of the microscope means with sufficient energy to kill unwanted cells; and selectively attenuating the beam such that cells to be saved are not irradiated with the unattenuated beam.

Finally the present invention relates to a preferred method for sorting a heterogeneous population of cells into a segregated population based upon physical or chemical properties or process capabilities by selectively killing unwanted cells which comprises:

providing a cell sorting apparatus including a microscope with an objective for viewing a heterogeneous population of cells fixed on a plate positioned adjacent the objective on a coordinate scanning or an individual cell-by-cell scanning basis;

drive means for moving the plate and container beneath the objective or for moving the objective or beam across the plate in an x-y coordinate plane or both such that the objective scans and views each of the cells in the heterogeneous population;

detection means for distinguishing an individual cell based upon a particular chemical or physical property or dynamic process determined by the detection means through the objective;

focussed radiant energy beam generating means with lenses and mirrors positioned for directing the beam in a path through the objective at an individual cell or a series of cells viewed by the objective;

attenuator means moveable into the path of the coherent light beam for selectively attenuating the beam to render it non-lethal to the cells;

controlled means for selectively providing the attenuator means into the path of the beam, wherein the detection means distinguishes cells to be saved when the attenuation means is positioned between the objective and the beam and wherein the attenuator means is removed from the path of the beam by the controlled means in order to kill the unwanted cells;

sorting the cells by selectively allowing the laser to kill unwanted cells by removal of the attenuator means from the beam.

SPECIFIC DESCRIPTION

OPTICAL SYSTEM

Figure 2:
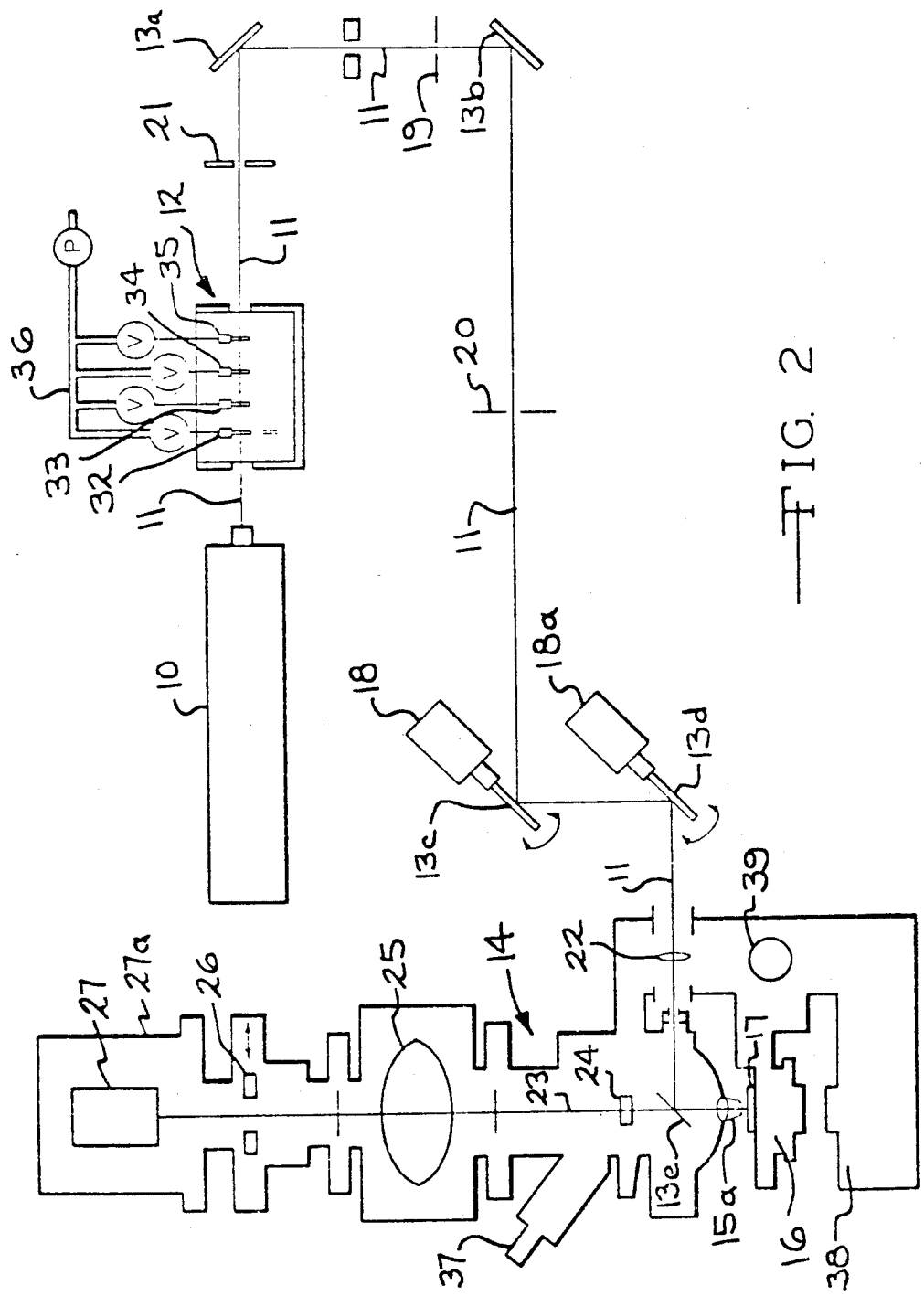
FIG. 2 is a schematic view of the laser (10), beam attenuator (12) and microscope means (14) in the preferred apparatus of the present invention.

Referring to FIGS. 1 and 2 a focussed radiant energy beam generating means, such as a laser 10, generates a beam 11. The laser 10 is preferably of the argon type and capable of generating light in wavelengths between about 300 and 560 manometers The beam 11 is filtered by beam attenuation means 12 provided in the path of the beam 11. Beam deflection means 13, such as mirrors 13a, 13b, 13c, 13d and 13e shown in FIG. 2, are used to provide the beam 11 inside a microscope 14. A focussed beam 15 is provided by an objective 15a. The focussed beam 15 measures about 1 micron in diameter compared to cells of a much greater dimension, for example 40 microns in diameter with nucleus of about 10 microns in diameter A microscope stage 16 supports plate 17 for supporting the immobilized cells (not shown). The stage 16 is moveable in an x and y plane perpendicular to the focussed beam 15. The mirrors 13c and 13d are moveable by motors 18 and 18a so as to provide scanning of the plate 17 in the x and the y plane by the focussed beam 15. If the stage 16 moves as described hereinafter, then the motors 18 and 18a are unnecessary. Diaphrams 19 and 20 can be used to regulate the beam as can shutter 21. Lens 22 contributes to movement of the beam 15 in the x or y coordinate without distortion when mirrors 13c and 13d are moved.

Mirror 13e is a dichromatic mirror such that emitted light 23 from the plate 17 passes through the mirror 13e. A barrier filter 24 allows only selected luminescence to pass. A mirror or grating element 25 is positioned in the path of the reflected light 23. A shutter 26 allows instantaneous passage of light to a photo multiplier tube 27.

The basic elements of the laser microscope apparatus (without the attenuator means 12 or the unique moveable stage 16 as discussed hereinafter) is described in detail in the Koppel article discussed previously. The laser is available from Lexel, Inc., Sunnyvale, Calif.; the microscope is available from Leitz, Inc., Rockleigh, N.J. and the moveable mirrors 13c and 13d are available from General Scanning, Inc., Waterstown, Mass.

The beam attenuation means 12 includes filters 28, 29, 30 and 31 which are moveable into and out of the beam 11 path by means of pneumatic actuators 32, 33, 34 and 35. Filter 28 is moved to position 28a out of the beam 11 path by the actuator 32 as shown by the dotted lines The remaining filters 29 to 39 are moved in the same manner. Valves V control the movement of the actuators 32 to 35. Pneumatic lines 36 provide air under pressure to valves V.

The microscope includes a conventional binocular viewing means 37, 38 and a manual adjustment knob 39.

Electronic Configuration

Figure 3:
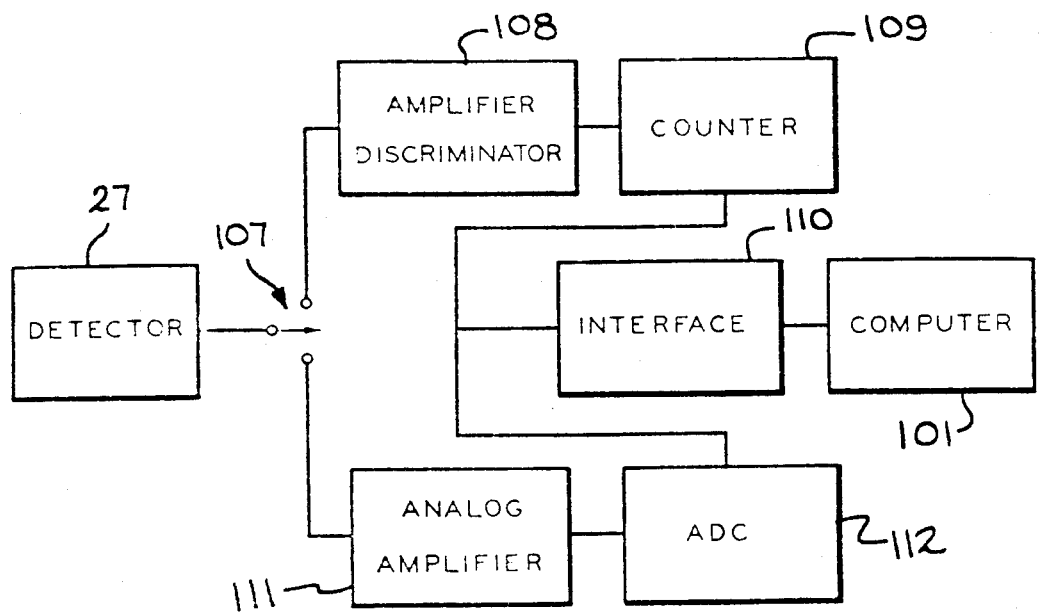
FIG. 3 is a block diagram showing the interface between the detector means (27) and the computer (101) in the preferred apparatus.

Referring to FIGS. 1 and 3, the electronic elements of the present invention are illustrated. The stage 16 is provided with electrically actuatable controls 100, as described more fully hereinafter, to provide movement of the stage 16 in the x-y plane perpendicular to the beam 11. Alternatively the motors 18 and 18a for mirrors 13c and 13d can be electrically moveable. The stage 16 movement is controlled by a computer 101 driven by a program in a disc(s) 102. The computer 101 can include video display 103 and recorder (not shown) connected to terminal 104. The microscope 14 functions as a fluoresence collection unit 105 from the stage 16. The photomultiplier tube 27 functions for fluorescence detection 106 and includes means 106a for counting and/or measuring the fluorescence which is recorded by the computer 101. Thus the computer 100 controls stage 16 movement and records the presence or absence of fluorescence on the plate 17. For slower operation a system without the computer 100 can be used; however with much less precision. The lens 15a provides beam 11 focussing, the mirrors 13a to 13e provide beam direction and the beam attenuator 12 provides beam attenuation as previously discussed.

In FIG. 3, the detector or photomultiplier tube 27 is coupled to the computer 101 by means of switch 107 to either: (a) an amplifer discriminator circuit 108 manufactured by Precision Products, Inc., Groton, Conn. and counter 109 through interface 110 to the computer 101; or (b) to a rate measuring circuit using the analog amplifer 111 and a 12 bit analog to digital converter 112. The digital output of this unit is fed to the computer 101 through the interface 110. All of this is state of art.

Cell Environmental Control

Figure 4:
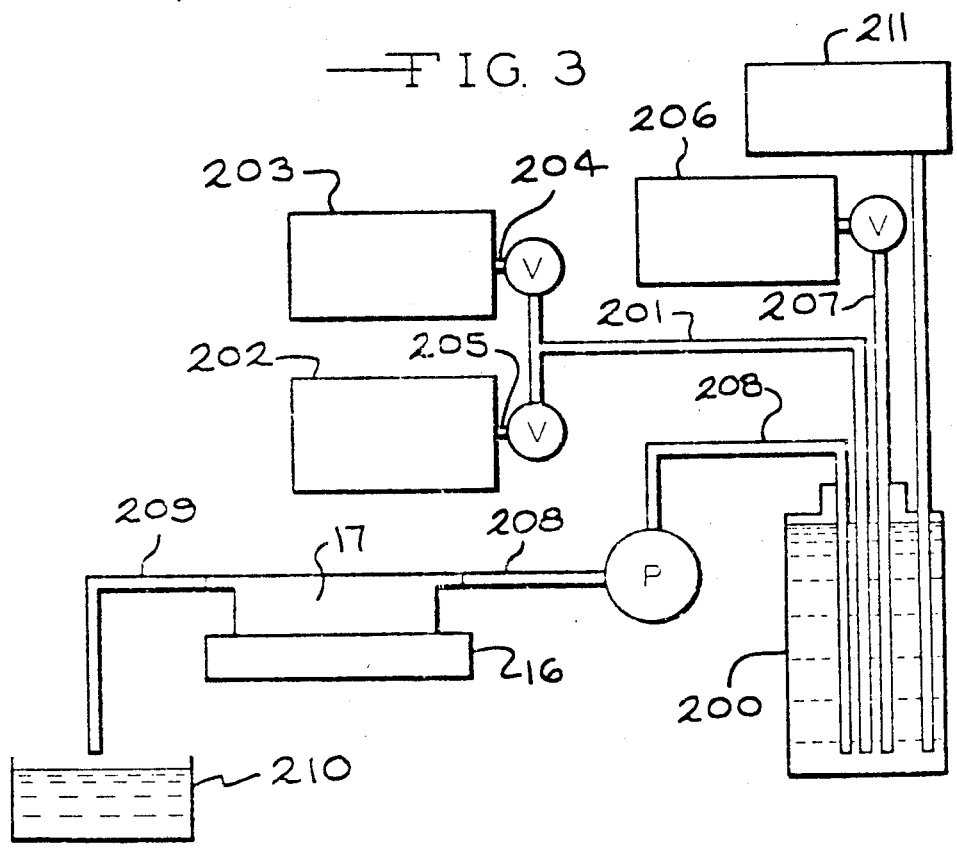
FIG. 4 is a schematic diagram showing preferred means for supplying a continuous flow of nutrient medium to cells on a plate (17) adapted to contain the medium

FIGS. 4, 5 and 6 show the plate 17 adapted for cell environmental control on stage 16. Container 200 is fed through line 201 with a mixture of cell growth media from containers 202 and 203 controlled by valves V in lines 204 and 205. Container 206 feeds necessary gases to container 200 through valve V in line 207. Pump P supplies the mixed media in container 200 and gases via line 208 to plate 17 as shown more fully in FIGS. 5 and 6. Line 209 releases spent media to a drain or waste container 210. Monitoring of media properties is accomplished by transducers sensitive to temperature, carbon dioxide, oxygen and hydrogen ion activity. These transducers are connected to unit 211.

The stage 16 includes motor 300 for movement in the x direction and by motor 301 for movement in the y direction. The movement is accomplished by screw shafts 300a and 301a. Attached by plates 302 and 303 to a first moveable holder 304 which slides in the x direction on base 305 and to a second moveable holder 306 which slides in the y direction on first holder 304. Such a stage is available from Ealing located in South Natick, Mass.

The second holder 306 is provided with a recess 306a adapted to receive the base 307a of a support 307. The support 307 has spaced apart recesses 307a and 307b and 307c adapted to receive a container 308 with inlet conduit 309 and outlet conduit 310 to be connected to lines 208 and 209 as shown in FIG. 4. The plate 308 includes integral pedestals 308a, 308b and 308c which support glass slides 311a, 311b and 311c which support the growing cells. The support 307 includes clips 312 for holding glass cover 313 in position on support 307 to completely cover the plate 308 when the cells are not being viewed by the objective 15a. During viewing of the cells on the slides 311a to 311c, the cover 313 is removed; however, the media is still allowed to flow across the container 308.

OPERATION

The present invention uses quantitative techniques for the characterization of diffusion in biological membranes whch has made it possible to employ laser technology to develop a scanning system capable of selecting a specific sub-population of cells based on a variety of structural and/or physical parameters. The cells do not move because they are supported on slides 311a to 311c and can be maintained in a state that is maximally advantageous to the maintenance of cell viability. The central idea of the approach is that cells with the desired property are spared from a pulse of high intensity laser beam 11 capable of destroying them. In this manner, a high level of cell enrichment for the defined characteristic is obtained. A significant feature of this system is that cells cultured on plates 17 may be used for enrichment. This advantage greatly increases the ultimate biological relevance of any information obtained by chemical analysis of the resulting sorted cells.

The intensity of the beam 11 is controlled by one or more neutral density filters 28 to 31 inserted or removed from the beam 11 path by air-driven solenoids 32 to 35 that are computer 101 controlled preferably in sixteen (16) discrete levels of attenuation. Filters can be optical, or acoustooptical or electrooptical. A series of diaphragms and mirrors 13a to 13e then guide the beam into the back of an incident-light fuorescence illuminator microscope 14 capable of epi-fluorescence illumination. The microscope objective 15a adjusts the final focus of the laser beam 15 at the cells. The dichroic mirror 13e reflects the laser beam 11 down through the miroscope 14 objective while allowing sample luminescence to be transmitted up to the photomultiplier tube 27 located in a thermoelectrically cooled housing 27a. The electronic shutter 26 placed in front of the tube 27 exacts to protect the tube 27 from high levels of irradiation. The signal from the tube 27 is fed to a computer 101 for processing and output.

The essential feature of positive cell selection is the maintenance of optimal growth conditions during the sorting cycle. The microflow container 308 provides a controlled environment for cells which can be further controlled by the computer 101 (not shown). This container 308 is preferably metallic and provides a thermal reservoir for temperature control, flow selection and regulating valves for media flow and gas mixing by the system shown in FIG. 4. This container 308 also provides for time dependent alterations, e.g. discrete growth substance addition, timed light exposure, etc. Sterility of growing cultures is maintained by the flow properties of the container 308. The immersion objective 15a is sterilized before use. Cells are grown in container 308 preferably with about one hundred forty-four $mm^2$ area continuously bathed by the flowing media.

For the purpose of cell sorting, three operational modes can be utilized. Cell sorting on the basis of a fluorescence marker recognition; cell sorting on the basis of a measured physical property; and cell sorting on the basis of a measured dynamic process (time dependent) characteristic.

The selection occurs as follows. The cells are grown on slides 311a to 311c. The edges of these slides 311a to 311c are coated with a strong fluorophore (not shown). A low intensity scout beam 15 traverses an (x) coordinate of the field. On its return on the same coordinate, the high intensity beam 11 is turned on. However, if luminescence were detected during the scout beam traverse, the beam 11 will be attenuated on its return pass. The positive detection of the differentiating signal by the tube 27 ensures the survival of the selected cells. Detection of the edge fluorophore on slides 311a to 311c serves as the boundaries for the scan field of the laser beam 11. The operator need only set the scout beam 11 on the plate 17. From this point, scanning of the total field is automatic and controlled by the computer 101.

The positive cell selection can be based upon measurements of physical properties such as endogenous fluorescence and de-polarization as well as marker recognition. For more sophisticated applications, actual short experiments can be performed after which selection may be based upon membrane parmeters such as rotational and/or translational differences and microviscosity. In all cases, these processes result in the isolation of a viable sub-population of cells or functional clones that have undergone selection without mechanical perturbations. The instrumentation for these types of measurements can be divided into three (3) groups which are modular in the progression from the simplest to the more complex.

Type I—This apparatus is designed to provide selection based upon the cell's affinity for an internally or externally directed site specific probe that is fluorescently labeled, e.g.-antibodies, lectins, DNA-RNA intercalating dyes. The basic components for this instrument are a tunable argon or argon-krypton laser 10, directing optics 13a to 13e and shutter 21, a microscope 14, a two-dimensional translating stage 16 and photon or rate counter 106a. The instrument is controlled by the computer 101.

Type II—The addition of incident and excitation polarizers and a monochrometer (not shown) in the emission beam before the photomultiplier tube 27 extends the capability of a Type I instrument to select on the basis of the polarization value of various fluorescently depolarizable dyes, e.g.—DPH, and also provide the researcher with the means to select cells that have altered fluorescence emission profiles for cell incorporated or adsorbed dyes. Selection is now based on actual changes in the physical state of the cell rather than purely as a function of the presence or absence of a structural component.

Type III—Since alterations in the membrane dynamics of cells have been demonstrated to be intimately involved in cellular activity, the type III instrument is designed to make its selection on the basis of a real time experiment evaluating lateral and/or rotational diffusion. This type of selection could not be performed on the flow separation system of the prior art due to the necessity for time resolved measurements. Because cells are plated and maintained in a viable environment, long term selections are feasible based on individual cellular experimentation. This type of instrumentation differs from type II primarily in the computer 101 software and data processing power.

Definable Parameters of Operation

Operator control is attained by keystroke command. In addition to initiating and terminating a sorting process, the following parameters can be scheduled under program control:

(a) two-dimensional stage 17 movement with step magnitude and frequency control.
(b) intensity of analytical (scout) and destroy beams 11.
(c) threshold beam intensity level.
(d) mode selection-marker or dynamic.
(e) threshold for positive response.
(f) single field scan or continuous mode of operation.
(g) control of all stage 17 operating functions:
  (i) temperature
  (ii) media mixing and flow
  (iii) gas injection
  (iv) growth control additives
  (v) light exposure
  (vi) auxiliary time dependent parameters.

Sorting analysis is now a major research technique in several disciplines, including cancer immunology, hematology, cell cycle analysis, pathology, biochemistry, general immunology, and quantitative cytology. New areas of interest for these methods are continuously emerging in cell biology, pharmacology, and toxicology, microbiology and cytogenetics. Diseases now under investigation with cell sorting technology are leukemia, lymphoma, and other cancers, infectious diseases, auto immune diseases, and genetic disorders. The apparatus of the present invention makes reliable cell selection possible for these investigations.

We claim:

1. A method for automatically sorting anchorage dependent cells by selective destruction of unwanted cells in situ comprising:
  (a) culturing a heterogeneous population of anchorage dependent cells on a support surface;
  (b) identifying wanted and unwanted cells by:
    (i) focussing a focussed radiant energy beam at a non-lethal energy level upon each cell, thereby eliciting a distinguishable response;
    (ii) monitoring the response with a discriminating means;
    (iii) determining the wanted from unwanted cells with a control means;
    (iv) selectively altering the intensity of a focussed radiant energy beam to a lethal energy level thereby destroying unwanted cells;
    (v) directing the movement of said lethal and said non-lethal beam means in relationship to said surface with an automatic coordinating means so as to impact all cells in a motion coordinated with said discriminating means and automatically adjusting said lethal means to destroy said unwanted cells.

2. An apparatus for automatically sorting anchorage dependent cells by selective destruction of unwanted cells in situ comprising:
  (a) a cell support surface;
  (b) a first focussed radiant energy beam selectively directed in a path intersecting said cell support surface, said first beam and said surface relatively moveable with respect to each other to access said beam to all cells attached to said surface;
  (c) discriminating means which monitors a response of said cells to said first beam at a non-lethal energy level;
  (d) a second focussed radiant energy beam adjusted selectively to alter the intensity of said second focussed radiant energy beam at a lethal energy level thereby destroying said unwanted cells;
  (e) control means which determines wanted from unwanted cells; and
  (f) automatic coordinating means selectively directing the movement of said beams in relationship to said surface so as to impact all cells with said beams in a motion coordinated with said discriminating means and automatically adjusting said beams to destroy said unwanted cells.

3. An apparatus in accord with the claim 2 in which said beams are laser beams.

4. An apparatus in accord with claim 2 in which the cell support surface is moveable in respect to said radiant energy beams and wherein said cell support is operably attached to environmental support means for life support of said cells on said support surface, and wherein movement and environment is controlled by said automatic coordinating means.

5. An apparatus in accord with claim 2, said discriminating means being a shielded photomultiplier tube observing said cells and sensing the response of said cells to said first focussed radiant energy beam to coordinate said response with the function of said automatic coordinating means.

6. An apparatus in accord with claim 5 in which said automatic coordinating means is computer directed.

7. The apparatus of claim 6 in which said automatic coordinating means is connected controllably to cell environment and flushing means in preservation of life support for said cells on said cell surface and in avoidance of residue from destroyed cells contamining remaining wanted cells.

8. An apparatus for automatically sorting anchorage dependent cells by selective destruction of unwanted cells in situ, the combination comprising:
  a cell support surface having connections for nutritional, thermal and chemical adjustment of cell environment;
  a focussed radiant energy beam having at least two energy intensities and directed in a path intersecting said cell support surface, said beam and said surface relatively moveable with respect to each other to access said beam to all cells attached to said surface;

cell discriminating means in an aligned relation with said beam and intersecting said cell surface in congruence with said beam and being correlated to said beam to first select a non-lethal energy intensity for recognition of wanted and unwanted cells, said discriminating means providing criteria for the selection of a second lethal energy intensity for said beam;

adjusting means providing the feedback control connection responsive to criteria provided by said discriminating means and selective of the energy intensity of said beam; and automatic coordinating means in control of movement of said beam in relation to said cell support surface in traversing the entire of said surface, automatically responsive to recognition by said discriminating means and shifting of said beam from non-lethal to lethal intensity by manipulation of said adjusting means, and selectively sustaining the environment of said cells on said support surface in preservation of cell life support conditions and the flushing of debris from said support surface during and after lethal exposure of unwanted cells on said support surface to said beam at lethal intensity.

* * * * *

UNITED STATES PATENT AND TRADEMARK OFFICE
CERTIFICATE OF CORRECTION

PATENT NO. : 4,629,687
DATED : 1986 December 16
INVENTOR(S) : Melvin S. Schindler, John F. Holland It is certified that error appears in the above-identified patent and that said Letters Patent is hereby corrected as shown below:

Column 1, line 63, insert a period after "sorting"

Column 1, line 66, insert a period after "fluorescence"

Column 2, line 29, insert a period after "surface"

Column 2, line 38, insert a period after "surfaces"

Column 2, line 53, insert a period after "cells"

Column 2, line 55, insert a period after "sorting"

Column 3, line 3, insert a period after "sorting"

Column 3, line 40, insert a period after "art"

Column 3, line 63, insert a period after "medium"

Column 5, line 44, insert a period after "manometers"

Column 5, line 53, insert a period after "diameter"

Column 6, line 16, insert a period after "lines"

Column 6, line 39, delete the hyphen after "and" (second occurrence)

UNITED STATES PATENT AND TRADEMARK OFFICE
CERTIFICATE OF CORRECTION

PATENT NO. : 4,629,687

DATED : 1986 December 16

INVENTOR(S) : Melvin S. Schindler, John F. Holland

It is certified that error appears in the above-identified patent and that said Letters Patent is hereby corrected as shown below:

Column 2, line 1, "mesurements" should read
--- measurements ---

Column 3, line 8, "electromagetic" should read
--- electromagnetic ---

Column 4, line 26, "processs" should read
--- processes ---

Column 5, line 61, "Diaphrams" should read
--- Diaphragms ---

Column 6, line 3, "photo multiplier" should read
--- photomultiplier ---

Column 7, line 34, "whch" should read --- which ---

Column 7, line 57, "fuorescence" should read
--- fluorescence ---

Column 7, line 62, "miroscope" should read
--- microscope ---

UNITED STATES PATENT AND TRADEMARK OFFICE
CERTIFICATE OF CORRECTION

PATENT NO. : 4,629,687
DATED : 1986 December 16
INVENTOR(S) : Melvin S. Schindler, John F. Holland It is certified that error appears in the above-identified patent and that said Letters Patent is hereby corrected as shown below:

Column 8, line 44, "parmeters" should read
--- parameters ---

Signed and Sealed this

Tenth Day of March, 1987

Attest:

DONALD J. QUIGG

Attesting Officer

Commissioner of Patents and Trademarks